US00PP15206P2

(12) United States Plant Patent
McNaughton

(10) Patent No.: US PP15,206 P2
(45) Date of Patent: Oct. 5, 2004

(54) ***LAVANDULA* PLANT NAMED 'LAVANG 38'**

(50) Latin Name: *Lavandula angustifolia*
Varietal Denomination: Lavang 38

(76) Inventor: Virginia McNaughton, Lavender Downs, Lawford Road, West Melton, RD6 Christchurch (NZ)

( * ) Notice: Subject to any disclaimer, the term of this patent is extended or adjusted under 35 U.S.C. 154(b) by 0 days.

(21) Appl. No.: 10/663,851

(22) Filed: Sep. 15, 2003

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—S B McCormick-Ewoldt

(57) ABSTRACT

A new cultivar of *Lavandula* plant named 'Lavang 38' that is characterized by vibrant violet-blue corollas, and low-growing compact bushy habit. These traits set it apart from all other existing varieties of *Lavandula* known to the inventor.

2 Drawing Sheets

Genus: *Lavandula.*
Species: *angustifolia.*
Denomination: Lavang 38.

BACKGROUND OF THE INVENTION

The present invention relates to a new and distinct cultivar of lavender known botanically as *Lavandula angustifolia* and hereinafter referred to by the cultivar name 'Lavang 38'. The new invention is a selected seedling from a group of seedlings produced by the open pollination between *Lavandula angustifolia* 'Midhall' (unpatented) and an unidentified *Lavandula angustifolia* cultivar. The female parent plant is 'Midhall' and the male parent plant is an unidentified cultivar of *Lavandula angustifolia.* 'Lavang 38' was discovered by the inventor in a cultivated area of Christchurch, New Zealand in 1995.

The new lavender 'Lavang 38' is distinct and was selected for compact bushy habit, flower spike colour, and striking presence. 'Lavang 38' is distinguishable from the parent plant, and all other existing varieties known to the inventor, by colour and size of spike, positioning of peduncles, foliage colour, shape of plant, and low growing habit.

The new variety 'Lavang 38' was first asexually propagated by the inventor in Christchurch, New Zealand in 1997 using soft to semi-hardwood cuttings. Since that time subsequent generations have been determined fixed, stable and true to type.

SUMMARY OF THE INVENTION

The following traits have been repeatedly observed and represent the distinguishing characteristics of the new *Lavandula* cultivar 'Lavang 38'. These traits in combination distinguish 'Lavang 38' from all other existing varieties of *Lavandula* known to the inventor. 'Lavang 38' has not been tested under all possible conditions and phenotypic differences may be observed with variations in environmental, climatic, and cultural conditions, however, without any variance in genotype.

1. *Lavandula* 'Lavang 38' exhibits a compact, bushy habit.
2. *Lavandula* 'Lavang 38' exhibits a combination of violet-blue corollas and violet calyx colour.

3. *Lavandula* 'Lavang 38' exhibits a low height for a *Lavandula angustifolia* cultivar.
4. *Lavandula* 'Lavang 38' is particularly floriferous when pruned and fed correctly.
5. *Lavandula* 'Lavang 38' is hardy to USDA Zone 5.

BRIEF DESCRIPTION OF THE DRAWINGS

The accompanying color drawings illustrate the overall appearance of the new cultivar 'Lavang 38' showing colors as true as it is reasonably possible to obtain in colored reproductions of this type. Colors in the drawings may differ from the color values cited in the detailed botanical description, which accurately describe the actual colors of the new variety 'Lavang 38'. The drawings illustrate 3-year-old plants growing out-of-doors in the ground in Christchurch, New Zealand.

The drawing labeled as

The drawing labeled as

Figure 1:
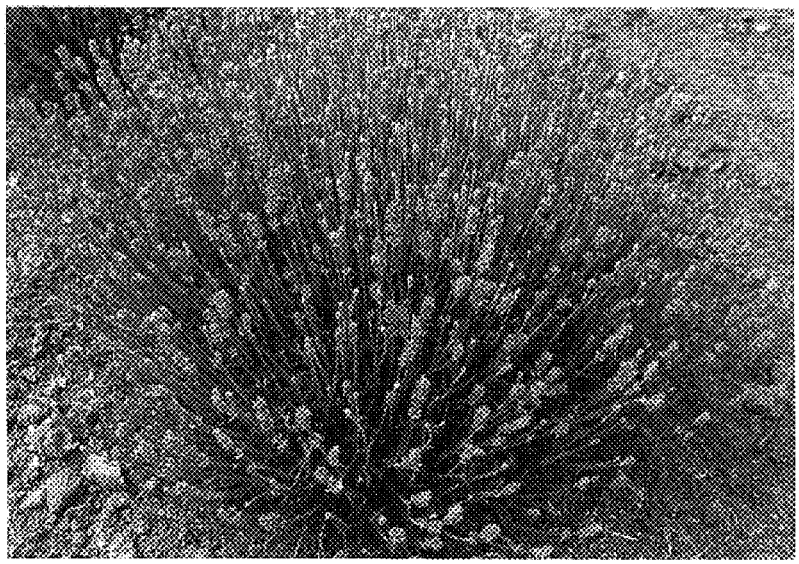
FIG. 1 shows the entire plant from an above and side view perspective, illustrating the plant habit and the flower spikes while in bud.
Figure 2:
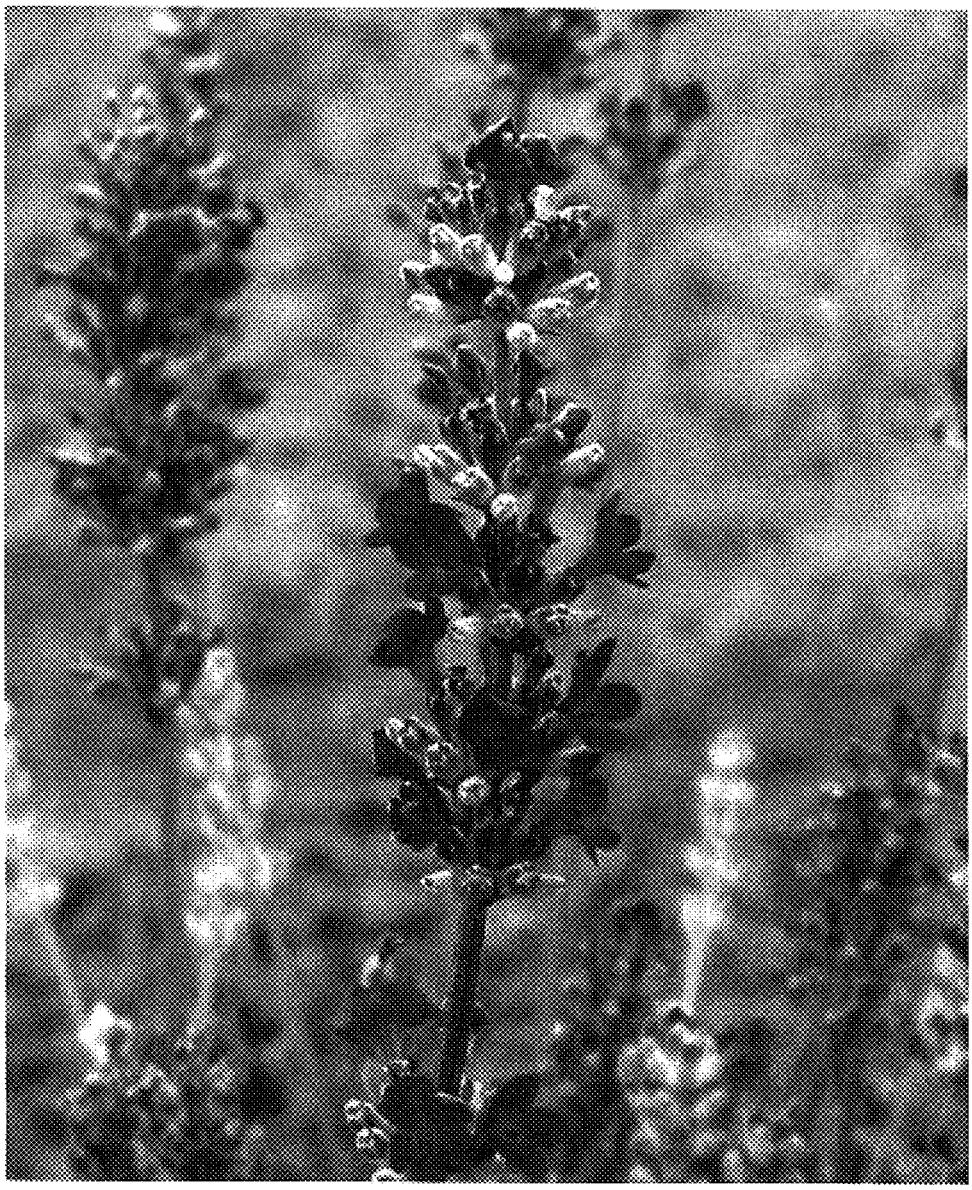

FIG. 2 shows a close-up on the flower spike, with individual flower buds and flowers open.

Both drawings are made using conventional photographic techniques and although colors may appear different from actual colors due to light reflectance, they are as accurate as possible by conventional photography.

BOTANICAL DESCRIPTION OF THE PLANT

The following is a detailed description of the new *Lavandula angustifolia* cultivar named 'Lavang 38'. Data was collected in West Melton, Canterbury, New Zealand from plants grown in the open ground and in dry conditions. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. Color determination using The Royal Horticultural Society Colour Chart was conducted using the light box at The New Zealand Plant Variety Rights Office at Lincoln, Canterbury, New Zealand. Please note that the brown, green and violet range in these charts do not have an adequate color range to match that seen in lavender. The growing requirements are similar to the species and no disease problems have been observed.

Botanical classification: *Lavandula angustifolia* 'Lavang 38'.
Species: *angustifolia.*
Common name: Lavender.
Parentage: 'LAVANG 38' is a hybrid seedling that resulted from open pollination of the following parent plants:
*Female parent plant.*—*Lavandula angustifolia* 'Midhall' (unpatented).
*Male parent plant.*—Unidentified *Lavandula angustifolia* cultivar.
Type: Aromatic perennial shrub.
Use: Front of border, low hedging, potted or feature plant.
Growth rate: Average for a *Lavandula angustifolia* cultivar.
Habit: Bushy compact habit with ascending flower spikes.
Shape: Round.
Height: 40 cm in height.
Spread: Approximately 40 cm in width.
Hardiness: USDA Zone 5.
Disease susceptibility: In common with the species *Lavandula angustifolia*, Lavang 38 may be susceptible to Lavender leafspot (*Septoria lavandulae*) or to bacterial blast (*pseudomonas syringae*) or to Phoma if conditions are very wet or if plants are overwatered. Lavang 38 is not considered unusually or, in comparison with other known cultivars of the species, differently susceptible to any of these pathogens whose occurrence is more associated with adverse growing conditions.
Propagation method: Vegetative cuttings, tissue culture.
Root system: Fibrous.
Soil: Plant in well-drained soil.
Light levels: Plant in full sun.
Special needs: Prune after flowering to maintain shape — will continue to flower if left but will need pruning prior to winter. Pruning will enhance number of flowers the following season.
Time to initiate roots: 21 to 36 days are needed to develop roots on an unrooted cutting.
Time to develop to a one-gallon: 6 months is needed to produce a finished 1-gallon container from a rooted cutting.
Branching habit: Foliage branched, erect, upright and compact.
Seasonal interest: Vibrant violet flower spikes (large corollas) in June and July.
Stem:
*Stem shape.*—Square.
*Stem surface.*—Main stems can be glabrous or puberulent, side branches are puberulent.
*Stem color.*—165D (pale orange-brown).
*Stem size.*—1–3 mm in diameter.
Foliage:
*Arrangement.*—Semi-upright stems with whorls of leaves, arranged opposite along stem. A basal pair of leaves subtend each whorl of leaves. Regular arrangement of leaves along stems.
*Leaf division.*—Simple.
*Apices.*—Obtuse.
*Base.*—Truncate.
*Margins.*—Entire and markedly revolute.
*Leaf shape.*—Linear.
*Color of mature leaves* (*upper*).—188C (grey-green).
*Color of mature leaves* (*lower*).—188C (grey-green).
*Color of young leaves* (*upper*).—192B (pale green).
*Color of young leaves* (*lower surfaces*).—Too revolute to view.
*Upper and lower surfaces.*—Puberulent.
*Venation.*—Mid vein depressed on upper surface and protruding beneath, side veins noticeable on lower surface with magnification. Generally leaves too revolute to see lower surface veining.
*Internodes.*—1–15 mm in length.
*Foliar fragrance.*—Sweet.
*Petiole.*—Sessile.
*Length of mature leaves.*—Approximately 1–2 cm. in length.
*Width of mature leaves.*—0.8–1.5 mm. in width.
Flower: Spike.
*Type of inflorescence.*—Terminal spike.
*Size of inflorescence.*—1.5–6 cm in length and 1–2 cm in width.
*Shape of inflorescence.*—Cylindric with whorls of flowers arranged evenly along stem.
*Base whorl.*—2–4 cm below main spike.
*Peduncles.*—6–14 cm in height and 0.2–1 mm in width.
*Peduncle position.*—Semi-upright.
*Peduncle color.*—143A (green).
*Lateral branches on peduncle.*—Occasional semi-stalked laterals terminated with mostly one flower. These laterals may be on one side of the peduncle or on both sides.
*Flower shape.*—Tubular.
*Corolla.*—Two-lipped with upper lip 2-lobed and lower lip 3-lobed.
*Corolla color.*—88A (vibrant violet).
*Bud color.*—90A (bright violet-blue).
*Calyx color.*—90A (bright violet-blue).
*Calyx surface.*—Puberulent to densely pubescent.
*Bracteoles.*—Present but insignificant.
*Bracteole length.*—0.5 mm.
*Fertile bract size.*—Small, approximately 2 mm wide and 1.5 mm long.
*Sterile bracts.*—Not present.
*Fragrance.*—Unusual scent but sweet, slightly reminiscent of unscented soap.
*Blooming period* (*New Zealand*).—December and January.
*Blooming period* (*U.S.A.*).—June and July.
Reproductive organs: Stamens: 4.
*Stamen length* (*2 posterior*).—2 mm.
*Stamen length* (*2 anterior*).—1 mm.
*Pistil.*—1.
*Pistil length.*—5 mm.
*Pistil diameter.*—Less than 0.25 mm.
*Filament diameter.*—Less than 0.25 mm.
*Filament color.*—Grayish-white.
*Style length.*—4 mm.
*Style color.*—Grayish-white.
*Stigma shape.*—Oval.
*Stigma color.*—Gray.
*Ovary shape.*—Slightly oblong to globose.

*Ovary dimensions*.—Too small to match, but approximately 0.5 mm long and 0.5 mm wide.
*Ovary position*.—Superior.
*Ovary color*.—Green.
*Anther shape*.—Reniform.
*Anther length*.—Less than 0.5 mm.
*Anther color*.—Dark brown to black.
*Pollen amount*.—Sparse.
*Pollen color*.—Orange.

Seeds:
*Number of seeds*.—2 per calyx.
*Colour of seeds*.—N200A.
*Length of seeds*.—1–2 mm. in length.

I claim:

1. A new and distinct variety of *Lavandula* plant named 'Lavang 38' as described and illustrated.

* * * * *